US00PP31216P2

(12) United States Plant Patent
Hansen

(10) Patent No.: US PP31,216 P2
(45) Date of Patent: Dec. 10, 2019

(54) **X *MANGAVE* PLANT NAMED 'DREADLOCKS'**

(50) Latin Name: ***Manfreda* times *Agave*, known as x *Mangave***
Varietal Denomination: Dreadlocks

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,480

(22) Filed: Nov. 20, 2018

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt

(57) ABSTRACT

A new and unique x *Mangave* plant named 'Dreadlocks' characterized by a medium mound of broad, semi-fleshy, longitudinally folded, grey-green foliage that is cascading or arches with age. The foliage has greyed-purple spots that intensify with strong ultraviolet light. Leaves have small, flexible marginal teeth. The new plant is suitable for the garden or as a potted plant in the garden or home.

1 Drawing Sheet

Botanical classification: hybrid; *Manfreda* times *Agave*, known as x *Mangave*.
Variety denomination: 'Dreadlocks'.

STATEMENT REGARDING PRIOR DISCLOSURES UNDER 37 CFR 1.77(B)(6)

The first public disclosure of the claimed plant, in the form of a sale, was made by Walters Gardens, Inc. on Nov. 27, 2017 to Plant Delights Nursery, Inc. in a private sale. Plants for this sale were obtained from the inventor. No plants of x *Mangave* 'Dreadlocks' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* hybrid plant, x *Mangave* 'Dreadlocks' that was hybridized by the inventor at a wholesale perennial nursery in Zeeland, Mich., USA as a cross between an unreleased, unnamed, proprietary *Manfreda maculosa* x *Agave gypsophylla* (not patented) given the breeder code H10-02-01 as the female or seed parent times *Manfreda* 'Chocolate Chip' (not patented) as the male or pollen parent. The cross was performed on Mar. 27, 2014 and seeds were harvested and sown later in the fall of 2014. Through trials at the same nursery the plant was assigned the breeder code 14-17-2. The new plant has been successfully asexually propagated by sterile shoot-tip tissue culture at the same nursery in Zeeland, Mich. The asexual tissue culture propagation has been found to produce stable and identical plants that maintain all the unique characteristics of the original plant.

BRIEF SUMMARY OF THE INVENTION x *Mangave* 'Dreadlocks' differs from its parents as well as all other *Manfreda, Agave* and x *Mangave* known to the applicant. The female parent has foliage that is shorter and less linear, thicker in cross section, has smaller marginal teeth, leaves are more fibrous and succulent, with more significant mahogany spotting and less arching. The male parent is smaller in habit, has foliage that is shorter, narrower, less fibrous, and has less mahogany spotting and background. The nearest comparison plants are 'Spotty Dotty' U.S. Plant Pat. No. 29,917, 'Freckles and Speckles' U.S. Plant patent application Ser. No. 15/932,464, 'Mission to Mars' U.S. Plant Pat. No. 29,393 and 'Whale Tale' U.S. Plant patent application Ser. No. 15/932,526. 'Spotty Dotty' has smaller foliage in length and width, and lacks the coarsely sinuate margin and folding. The teeth on 'Spotty Dotty' are also less flexible. 'Freckles and Speckles' has a slightly more ovate leaf with the widest part near the middle of the leaf and has little to no folding up of the margins and slightly less flexible marginal teeth. 'Mission to Mars' is larger in leaf and habit with more intense reddish coloration in the foliage and less marginal folding and no sinuate margin. 'Whale Tale' has more bluish glaucous foliage, less greyed-purple spotting, less marginal folding and less sinuate margin. The marginal teeth on 'Whale Tale' are more pronounced and firmer. 'Mint Chocolate Chip' U.S. Plant Pat. No. 29,343 is smaller in habit, has more folded leaves with more grayish green foliage with less overlapping mahogany spotting.

The new plant, 'Dreadlocks', is unique from all of the above cultivars and all *Agave*, x *Mangave* and *Manfreda* known to the inventor by the following combined traits:

1. Medium mound of medium grey-green lanceolate, broad, semi-fleshy, longitudinally-folded, coarsely-sinuate foliage;
2. Foliage has greyed-purple spots that become more pronounced in strong ultraviolet light;
3. Leaf margins have small, flexible, marginal teeth;
4. Moderate growth rate.
5. Foliage cascades or arches with age.

BRIEF DESCRIPTION OF THE DRAWING

The photograph of x *Mangave* 'Dreadlocks' demonstrates the overall appearance of the new plant including the unique traits as a three-year-old plant grown in a trial garden with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
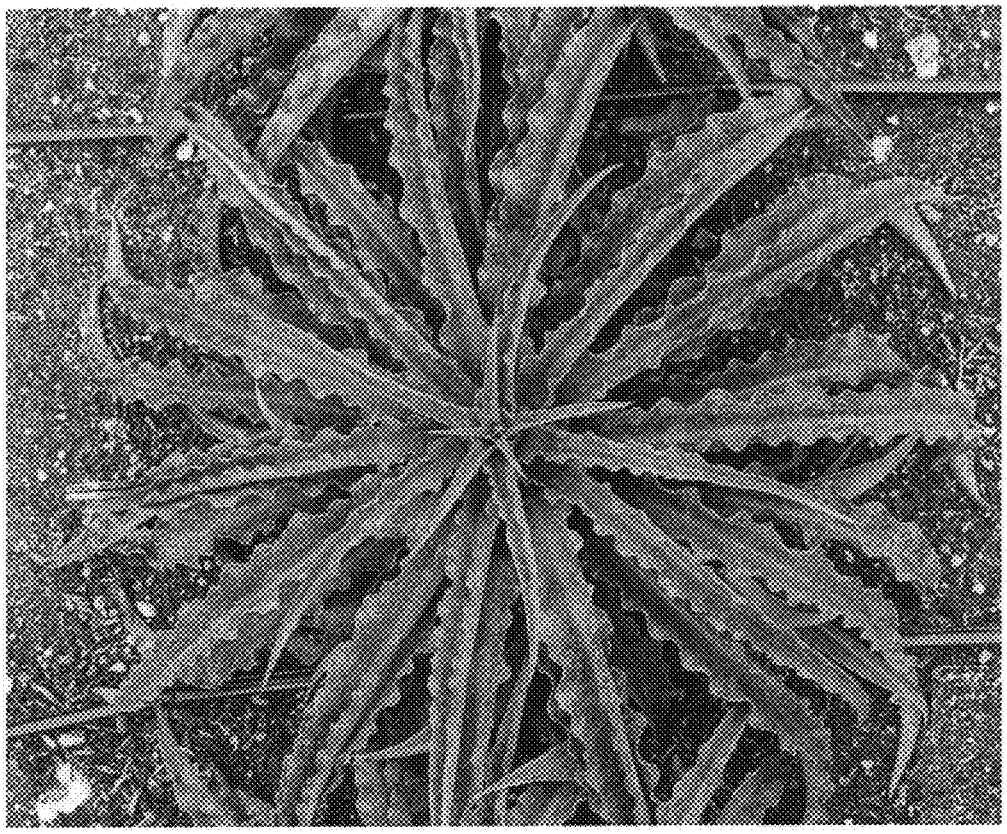
FIG. 1 shows a top view of a three-year-old plant in a full-sun trial garden.
Figure 2:
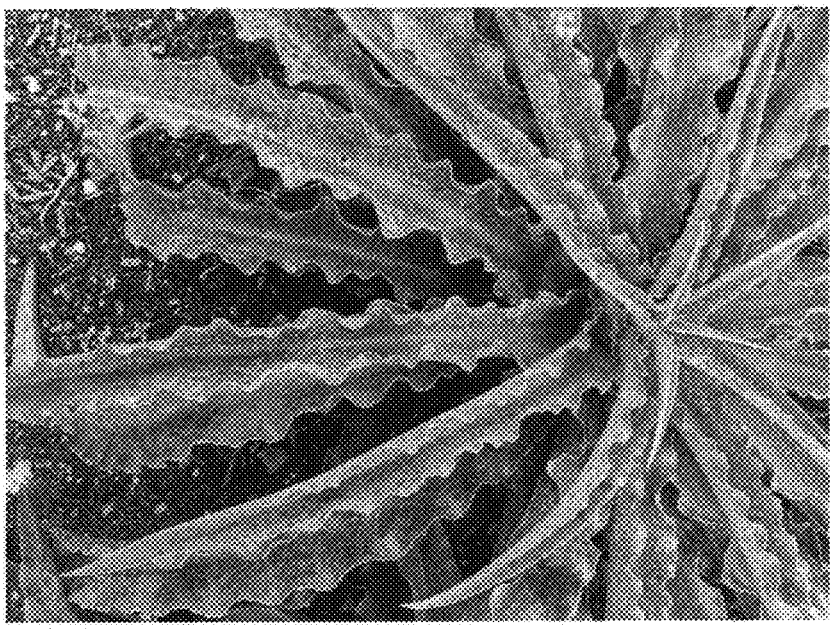
FIG. 2 shows a close-up of the foliage of a two-year-old plant with sinuate margins and heavily folded leaves with small teeth.

The following descriptions and color references are based on the 2015 edition of The Royal Horticultural Society Colour Chart except where common dictionary terms are used. The new plant, x *Mangave* 'Dreadlocks', has not been observed under all possible environments. The phenotype may vary slightly with different environmental conditions, such as temperature, light, fertility, moisture and maturity levels, but without any change in the genotype. The following observations and size descriptions are of a two-year-old plant in a commercial wholesale greenhouse in Zeeland, Mich. with supplemental water and fertilizer as needed.

Parentage: H10-02-01, an unnamed select form of *Manfreda maculosa* times *Agave gypsophylla* as female or seed parent and 'Chocolate Chip' as the male or pollen parent;

Propagation: By sterile shoot-tip tissue culture;

Time to initiate roots from tissue culture: About 21 days;

Growth rate: Moderate;

Crop time: About 12 to 15 weeks to finish in a 3.8 liter container from a 35 mm tissue culture growing at about 21° C.;

Rooting habit: Fleshy, lightly branching, with roots up to 20 cm long;

Root color: Nearest RHS 158C;

Plant shape and habit: Succulent herbaceous perennial with basal rosettes of about 40 leaves radially emerging outwardly from central stem, producing a radially-symmetrical, rounded mound;

Plant size: Foliage height about 22.0 cm tall from soil line to the top of the leaves and about 60.0 cm wide at the widest point slightly below soil line in container or at the soil line in test garden;

Foliage description: Lanceolate; simple; sessile; bi-laterally symmetrical; apex narrowly acute with terminal spine; soft terminal spine to about 5.0 mm long; base truncate; conduplicate; margins coarsely sinuate, average distance between waves about 3.0 cm; margins finely dentate with soft flexible teeth; glabrous and glaucous abaxial and adaxial; with abaxial and adaxial spots about 2.0 mm to 7.0 mm long and wide frequently touching or overlapping especially toward proximal center;

Teeth: Flexible; about 1.0 mm long and 1.0 mm wide at base of tooth and about 4.0 mm apart on mature leaves;

Leaf size: To about 45.0 cm long, about 8.2 cm wide toward base when flattened, about 2.5 cm deep; about 4.0 mm thick at basal midrib; average about 38.0 cm long, 8.0 cm wide and 4.0 mm thick;

Foliage fragrance: None observed;

Leaf number: About 40 per plant;

Leaf blade color:

*Adaxial* (*young*).—Nearest blend between RHS N138C and RHS N138D with spots nearest RHS 189A in low ultraviolet light intensifying with high ultraviolet exposure to nearest RHS N187A.

*Abaxial* (*young*).—Nearest blend between RHS N138C and RHS 189B with spots nearest RHS 189A in low ultraviolet light intensifying with high ultraviolet exposure to nearest RHS N187A.

*Adaxial* (*mature*).—Variable, nearest RHS NN137C distally and nearest RHS 137B proximally with spotting of nearest RHS N186B.

*Abaxial* (*mature*).—Between RHS N138B and RHS 137C with spots between RHS N187A and RHS N187B.

*Teeth*.—Between RHS N170D and RHS N155D.

*Terminal spine*.—Nearest RES 197A.

Petiole: Leaves sessile;

Veins: Parallel; not distinct abaxial or adaxial;

Flower description: Not yet observed;

Fruit and seed not observed;

Disease resistance: X *Mangave* 'Dreadlocks' has not been observed to be resistant to diseases beyond that which is normal for x *Mangave, Agave* or *Manfreda*. The new plant is xeromorphic and survives well with minimal water once established. The new plant is estimated to be hardy at least from USDA zone 9. Full extent of winter hardiness has not been tested.

It is claimed:

1. A new and distinct cultivar of ornamental x *Mangave* plant named 'Dreadlocks' as herein described and illustrated.

* * * * *